(12) United States Patent
Chakraborty et al.

(10) Patent No.: US 8,775,097 B2
(45) Date of Patent: *Jul. 8, 2014

(54) AUTOMATED DECISION SUPPORT FOR ASSOCIATING AN UNKNOWN BIOLOGICAL SPECIMEN WITH A FAMILY

(71) Applicant: University of Tennessee Research Foundation, Knoxville, TN (US)

(72) Inventors: Ranajit Chakraborty, Fort Worth, TX (US); John Douglas Birdwell, Oak Ridge, TN (US); Tse-Wei Wang, Oak Ridge, TN (US); Dale V. Stansberry, Oak Ridge, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 66 days.

This patent is subject to a terminal disclaimer.

(21) Appl. No.: 13/633,940

(22) Filed: Oct. 3, 2012

(65) Prior Publication Data

US 2013/0041594 A1 Feb. 14, 2013

Related U.S. Application Data

(63) Continuation of application No. 12/684,539, filed on Jan. 8, 2010, now Pat. No. 8,301,392, and a continuation-in-part of application No. 11/467,834, filed on Aug. 28, 2006, now Pat. No. 8,271,201.

(60) Provisional application No. 61/193,927, filed on Jan. 9, 2009, provisional application No. 60/836,941, filed on Aug. 11, 2006.

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS

| | | |
|---|---|---|
| 6,741,983 B1 | 5/2004 | Birdwell et al. |
| 7,162,372 B2 | 1/2007 | Wang et al. |
| 7,272,612 B2 | 9/2007 | Birdwell et al. |
| 7,454,411 B2 | 11/2008 | Birdwell et al. |
| 7,624,087 B2 | 11/2009 | Birdwell et al. |
| 7,640,223 B2 | 12/2009 | Birdwell et al. |
| 2003/0232356 A1 | 12/2003 | Dooley et al. |
| 2004/0126803 A1 | 7/2004 | Cash et al. |
| 2005/0176031 A1 | 8/2005 | Sears et al. |
| 2009/0228245 A1 | 9/2009 | Gilbert et al. |

OTHER PUBLICATIONS

Fung, User-friendly programs for easy calculations in paternity testing and kinship determinations, 2003, Forensic Science International, vol. 136, pp. 22-34.*

Egeland et al., Beyond traditional paternity and identification cases Selecting the most probably pedigree, 2000, Forensic Science International, vol. 110, pp. 47-59.*

Budowle et al., Review Article, Forensic aspects of mass disasters: Strategic considerations for DNA-based human identification, 2005, Legal Medicine, No. 5, pp. 230-243.*

Cowell et al., A clustering algorithm using DNA marker information for sub-pedigree reconstruction, 2003, Journal of Forensic Science, 48(6): pp. 1239-1248.*

R. C. Elston, et al., "A General Model for the Genetic Analysis of Pedigree Data," Human Heredity 21: pp. 523-542, 1971.

Frank Dudbridge, "A survey of current software for linkage analysis," Human Genomics, vol. 1, No. 1, Nov. 2003, pp. 63-65.

Soledad A. Fernandez, et al., "Sampling genotypes in large pedigrees with loops," Genet. Sel. Evol. 33, 2001, pp. 337-367.

C. Cannings, et al., "The Recursive Derivation of Likelihoods on Complex Pedigrees," Advances in Applied Probability, vol. 8, No. 4, Dec. 1976, pp. 622-625.

B. Leclair et al., "Application of Automation and Information Systems to Forensic Genetic Specimen Processing," Future Drugs Ltd., Mar. 2005, pp. 241-250.

K. L. Monson et al., "The mtDNA Population Database: An Integrated Software and Database Resource for Forensic Comparison," Forensic Science Communications, Apr. 2002, pp. 1-6.

F. V. Jensen et al., "Bayesian Updating in Causal Probabilistic Networks by Local Computations," Computational Statistics Quarterly, 1990, pp. 269-282.

S. M. Edson et al., "Naming the Dead—Confronting the Realities of Rapid Identification of Degraded Skelatal Remains," Central Police University Press, 2004, pp. 64-89.

D. J. Spiegelhalter et al., "Statistical Reasoning and Learning in Knowledge-bases Represented as Causal Networks," Springer-Verlag, 1988, pp. 105-112.

L. Roewar et al., "Online Reference Database of European Y-Chromosomal Short Tandem Repeat (STR) Halotypes," Forensic Science International, 2001, pp. 106-113.

(Continued)

*Primary Examiner* — Jason Sims
(74) *Attorney, Agent, or Firm* — Cameron LLP

(57) ABSTRACT

Three methods of predicting whether an unknown biological specimen of a missing person originates from a member of a particular family comprise an initial automated decision support (ADS) algorithm for determining a list of relatives of the missing person for DNA typing and which typing technologies of available technologies to use for a listed relative. The ADS algorithm may be implemented on computer apparatus including a processor and an associated memory. The ADS method comprises determining a set of relatives of available family member relatives for DNA typing via a processor from a stored list of family member relatives according to one of a rule base, a table of hierarchically stored relatives developed based on discriminatory power or by calculating the discriminatory power for available family relatives to type. The ADS method may further comprise comparing at least one set of DNA typing data for the unknown biological specimen to DNA typing data from biological specimens from the determined set of relatives; calculating by the processor a likelihood function that the person is related to the family; and outputting a decision whether or not the person is related to the family.

13 Claims, 7 Drawing Sheets

(56) References Cited

OTHER PUBLICATIONS

Frederick R. Bieber et al., "Finding Criminals Through DNA of Their Relatives," Science, Jun. 2, 2006, pp. 1315-1316.

Author Unknown, DNA.VIEW 2006 User's Manual, Apr. 28, 2006, version 27.26, pp. 1-328.

E. S. Lander et al., "Construction of Multilocus Genetic Linkage Maps in Humans," Proceeedings of the National Academy of Sciences of the United States of America, vol. 84, No. 8, Apr. 15, 1987, pp. 2363-2367.

L. G. Biesecker et al., DNA Ientification Afte the 9/11 World Trade Center Attack, Scince Magazine, Nov. 18, 2005, pp. 1122-1123.

C. H. Brenner, "Some Mathematical Problems in the DNA Identification of Victims in the 2004 Tsunami and Similar Mass Fatalities," Forensic Science International, Dec. 19, 2005, pp. 172.180.

H. D. Cash et al., Development Under Extreme Conditions: Forensic Bioinformtics in the Wake of the World Trade Center Disaster, Pacific SYmposium on Biocomputing, Stanford University, 2003, pp. 638-653.

F. Dudbridge, "A Survey of Current Software for Linkage Analysis," Human Genomics, Nov. 2003, vol. 1, No. 1, pp. 63-65.

D. R. Nyholt, "All LODs Are Not Created Equal," American Journal of Human Genetics, vol. 67, 2000, pp. 282-288.

\* cited by examiner

AUTOMATED DECISION SUPPORT FOR ASSOCIATING AN UNKNOWN BIOLOGICAL SPECIMEN WITH A FAMILY

This application is a continuation of U.S. patent application Ser. No. 12/648,539 filed Jan. 8, 2010 (now allowed) which is a continuation-in-part of U.S. patent application Ser. No. 11/467,834 filed Aug. 28, 2010 (now U.S. Pat. No. 8,271,201 issued Sep. 18, 2012) which claims the benefit of U.S. Provisional Application Ser. No. 60/836,941 filed Aug. 11, 2006, and further claims the benefit of U.S. Provisional Application Ser. No. 61,193,927, filed Jan. 9, 2009, all of which applications are incorporated herein by reference as to their entire contents.

TECHNICAL FIELD

The technical field of embodiments of the present invention relates to methods of searching for, ranking, and identifying missing individuals using DNA profiles and DNA database search techniques including automated decision support for identifying family members of the missing individuals for DNA typing and associating an unknown biological specimen with a family.

BACKGROUND OF THE TECHNICAL ART

Identification of a biological sample using DNA profiles is an important task in forensic science. For example, the terrorist attacks of Sep. 11, 2011 placed huge demands on forensic scientists to identify human remains from the collapsed World Trade Center buildings. In light of these demands, forensic scientists need more efficient and more accurate search methods to assist in identifying biological specimens by using DNA typing technologies to obtain DNA profile data.

Ideally, a forensic scientist obtains a DNA profile from a sample obtained from a personal effect of a missing person such as a toothbrush, razor, or comb, and searches for a match in a database containing DNA profiles from unknown biological specimens of a missing person or victim's remains. In theory, this approach can identify the missing person, but in practice, this approach breaks down when it encounters samples with partial profiles or when the reference origin of the personal effect cannot be obtained or verified. It is common to obtain incomplete DNA profiles from disaster areas due to harsh environmental conditions where the DNA integrity has diminished. This forces forensic scientists to lower the match stringencies within database search engines, yielding potentially numerous false positives. In addition, incorrectly labeled personal effects can lead to inaccurate identifications.

When direct searching fails, identification using kinship analysis is often necessary. Kinship analysis comprises possibly narrowing the scope of a search by using any available DNA or non-DNA information to exclude unrelated specimens and then calculating genetic relatedness to at least one biological relative of a missing person. For example, the technology used for kinship analysis after the World Trade Center disaster of Sep. 11, 2001, relied on pair-wise comparison of a test DNA profile from an unknown biological specimen to a target DNA profile from a known biological relative, taking into account various familial relationships such as parent-child, sibling or half-sibling, and calculating the value of a function that indicates the likelihood or probability that the relationship is true (e.g., Cash et al., genecodesforensics.com/news/CashHoyleSutton.pdf, 2003). A likelihood ratio is commonly used, which indicates the likelihood that the given DNA profiles of the two samples would be obtained if they are related, relative to the likelihood or probability that these DNA profiles would be present if the individuals were unrelated. A measure of genetic similarity can also be used to indicate the likelihood that a relationship is true. Such a measure can, for example, account for shared DNA alleles, loss of genetic information through degradation of the DNA, or the possibility of mutation of an allele. For any of these functions, the specimens are then independently sorted according to the function's value. When a likelihood function, such as probability, likelihood, or likelihood ratio is used, the specimens are sorted according to the calculated likelihood function value that the DNA profile from an unknown biological specimen is related to the DNA profile from a biological relative. Unfortunately, this approach is cumbersome and imprecise for large cases, such as the World Trade Center disaster, because each search is for a specimen which is related to a single family member. A pair-wise comparison to the DNA profile of a single known relative can produce a large collection of candidate profiles. Human analysts must then sort, correlate, and analyze the matches, possibly manually with available meta data, which is a very labor intensive and time consuming process.

Software tools exist which allow the correlation of DNA match results from a single type of DNA profile, such as short tandem repeat (STR), single nucleotide polymorphism (SNP), mitochondrial DNA (mtDNA) and Y-STR DNA, among others. Technologies are needed which can use all available DNA profile information involving a missing individual or an unknown biological specimen and his/her relatives to further enhance the ability to make an accurate identification.

SUMMARY OF THE EMBODIMENTS

Several embodiments are discussed herein which provide methods of associating an unknown biological specimen with a particular family. Automated decision support may aid forensic scientists to select enough and the correct individuals related to a missing person, disaster victim or other remains for DNA typing. The relative importance of different combinations of relatives to a missing person and of different combinations of DNA typing technologies is used in automated decision support to replace guess work for selecting relatives to type and DNA typing technology processes to be used for typing a given selected relative. Automated decision support for selecting family relatives to a missing person maximizes the relative likelihood of obtaining a high probability of obtaining a correct match between a missing person and a family. The output of the process may be a pedigree likelihood ratio (PLR) based on the totality of selected multiple relatives' DNA profiles.

In one embodiment, there is provided a computer-implemented method of selecting and typing a subset of available family members for DNA typing according to a selected DNA typing technology to a missing person to identify or exclude a typed unknown biological specimen for implementation on computer apparatus. The computer apparatus includes a processor, an input device coupled to the processor, an output device coupled to the processor and a memory for storing profile data obtained from said typed unknown biological specimen, the memory being coupled to the processor. The computer-implemented method comprises: storing relationships in the memory between said missing person and the available family members in a pedigree via said input device; using the relative discriminating power of the pedigree with at least two combinations of the available family members to select a combination of available family members for DNA typing; using a selected DNA typing technology for typing the selected combination of available family members to obtain DNA profile data and storing said DNA profile data for the selected combination in the memory; using the pedigree and the stored DNA profile data of the selected combination to calculate a likelihood function value between the stored profile data obtained from the typed unknown biological specimen and the stored profile data for the selected combination of available family members via said processor; and outputting a decision whether the typed unknown biological specimen originates from the missing person and the pedigree or to exclude the typed unknown biological specimen as unrelated to the pedigree.

In another embodiment, there is provided a computer-implemented method of identifying an unknown biological specimen as likely related to a family comprising at least first and second available family member relatives. The method is implemented on computer apparatus comprising a processor having memory. The computer-implemented method comprises; determining a family pedigree for the unknown biological specimen of available family member relatives for DNA typing; using a rule base implemented as an application running on the computer apparatus to select a subset of available family members for DNA typing according to a selected DNA typing technology for each selected available family member; storing the family pedigree of the subset of available family members in the computer memory; obtaining and storing DNA typing data of the unknown biological specimen in the computer memory; obtaining and storing DNA typing data of the selected subset of available family members in the computer memory; using the family pedigree and said stored DNA typing data of the selected subset of available family members and the DNA typing data of the unknown biological specimen to calculate a likelihood function value between the stored DNA typing data obtained from the typed unknown biological specimen and the stored typing data for the selected subset of available family members via the processor; and outputting a decision whether the typed unknown biological specimen is related to the pedigree or to exclude the typed unknown biological specimen as unrelated to the pedigree.

In another embodiment, there is provided a computer-implemented method of supporting automated decision making for selecting relatives in a family related to a person for DNA typing to identify as related or exclude as unrelated a typed unknown biological specimen to the family. The method is implemented on computer apparatus comprising a processor having memory. The computer implemented method comprises: storing family pedigree information for the family composed of the relatives related to the person in memory; storing DNA typing data of the typed unknown biological specimen in the memory; determining a degree of degradation for the unknown biological specimen, the unknown biological specimen being taken from the person: if both parents of the person are available, then, select both parents for DNA typing and store DNA typing data for both parents according to a selected DNA typing technology in the memory; when one of the parents is unavailable and a child of the person is available, then, selecting the child for DNA typing along with the spouse of the individual; if one or both parents or a child is not available for DNA typing, selecting remaining available family relatives for typing according to a rule base; based on the degree of degradation of the remains and the rule base, obtaining and storing DNA typing data for selected family members according to the following hierarchy listed in order of most to least contribution of information obtainable about the person if the following family member or family members are available for typing: a spouse and two children; child, parent and spouse; two children; one full sibling and one child; one child and a spouse; two full siblings; one parent or one child; and one full sibling; storing the DNA profile data for the determined available family members in the memory; and using the family pedigree and the stored DNA typing data of a selected subset of available family members and the DNA typing data of the unknown biological specimen of the missing person to calculate a likelihood function value between the stored DNA typing data obtained from the typed unknown biological specimen and the stored typing data for the selected subset of available family members via the processor; and outputting a decision whether the typed unknown biological specimen originates from the missing person and the pedigree or to exclude the typed unknown biological specimen as unrelated to the pedigree.

Other embodiments comprise computer-readable media which store computer-executable instructions for performing any of the disclosed methods and computer apparatus for implementing the method.

BRIEF DESCRIPTION OF THE DRAWINGS

The present invention is illustrated by way of example, and not by way of limitation, in the figures of the accompanying drawings.

DETAILED DESCRIPTION OF THE EMBODIMENTS

Figure 1:
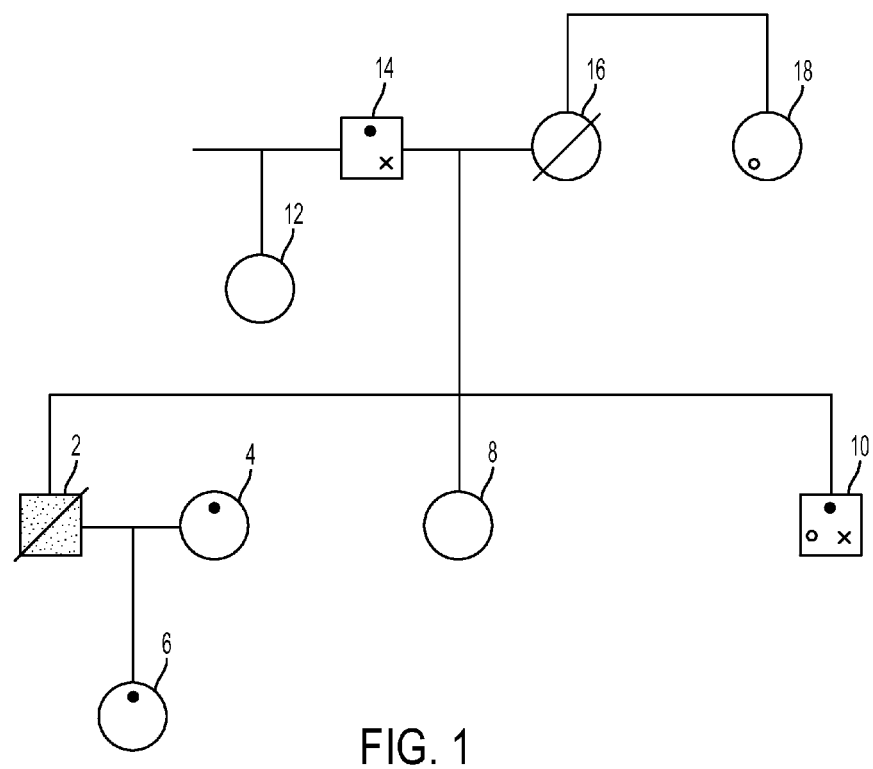
FIG. 1 is a first pedigree example showing family relative relationships to a missing relation.
Figure 3:
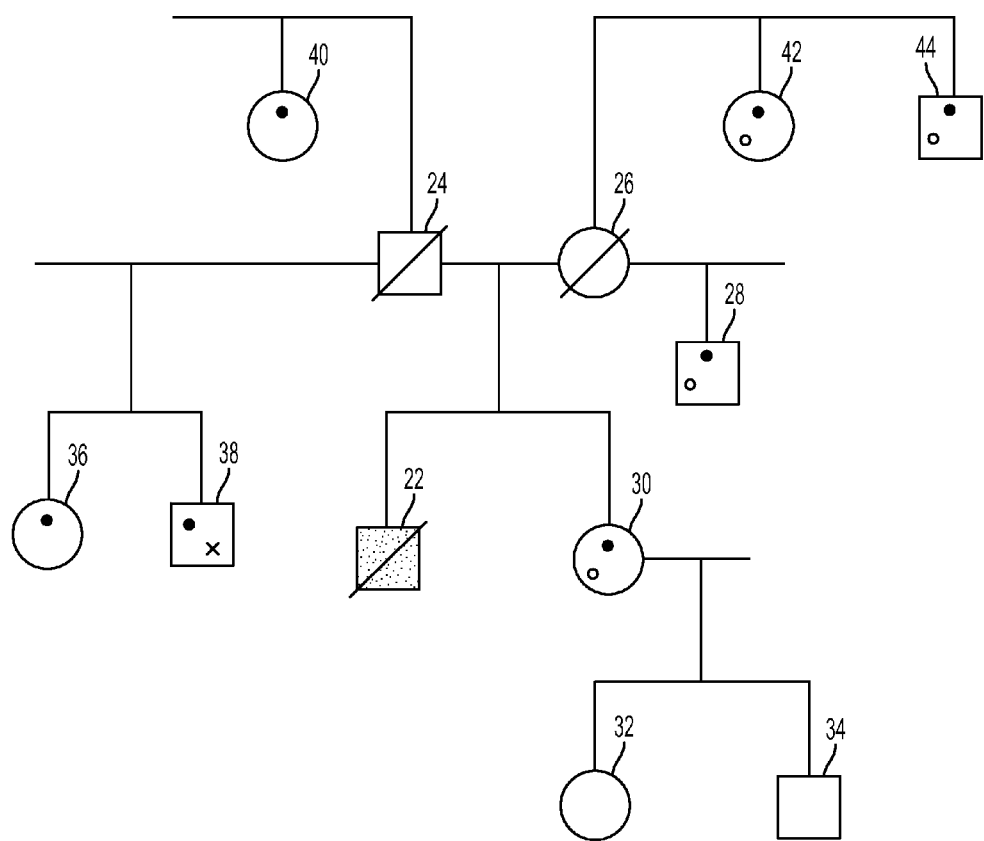
FIG. 3 is a second pedigree example showing blood relative relationships to a missing relation where both parents are deceased and no samples from them are available.

Automated Decision Support for Determining which Blood Relations to Type and which DNA Typing Technology to Use Automated decision support (ADS) may assist forensic scientists in kinship analysis to determine which blood relations or relatives to type from a set of available family members and relatives to a missing person. Determining who is missing is a first step, for example, in cases of a mass disaster, a common gravesite, war, terrorist attack or natural phenomenon among other causes of the finding of missing human and associated remains. A next step is developing a family pedigree of relations with available DNA for developing DNA profiles. ADS may eliminate guesswork in determining a reasonable minimum number of relatives of a family to DNA type from a large pool of relatives available where DNA typing comprises obtaining at least one test DNA profile of a relative. A pedigree likelihood ratio (PLR) can result from an ADS method implemented, for example, on a personal computer. Challenges may arise in deciding relations to type from a large pool, for example, where most important relatives or remains are unavailable or their DNA is completely degraded for example, where one or both parents are deceased or their artifacts from their personal use have been allowed to degrade over time (i.e. DNA samples left on articles of personal use). An ADS tool then may comprise a plurality of portions of a method and be embodied in the form of a single or plurality of computer apparatus or distributed systems. Thus, part or all of the ADS tool may be portable and used on location by inputting available kinship DNA and unavailable DNA and then, from the PLR analysis results, determining a reasonable list of relatives to type rather than, for example, typing every relative available. Using ADS, one may still obtain a high degree of matching to a missing person's DNA from fewer samples than by typing all available kin. In other words, ADS may determine a plurality of known family individuals to type and assess after a disaster has occurred. If there is a mixture of DNA as a human remain, the mixture may be resolved, for example, using the least square deconvolution methods described in U.S. Pat. No. 7,162,372, incorporated by reference as to its entire subject matter for mixture resolution. The possible contributors to the mixture, identified for example using the methods described in U.S. Pat. No. 7,162,372, can then be assessed against the DNA profiles of the individuals identified for typing by the ADS in the same manner as with single source specimens. Other known typing methods may be employed when DNA residuals exist in isolation from DNA of other missing persons, for example, when a mass grave site is discovered. Three DNA typing technologies are in current use in the forensic community: STR, Y-STR and mitochondrial DNA (mtDNA). A method and apparatus for allele peak fitting and attribute extraction from DNA sample data are described by Published U.S. Application Serial No. 2009/0228245 of Sep. 10, 2009. In FIGS. 1 and 3 herein, these three processes or technologies are represented as follows: STR is represented by a closed circle; mtDNA is represented by an open circle; and Y-STR is represented by an X. A fourth, SNP, is sometimes used and a fifth, miniSTR is becoming more common. All can have different rules of inheritance which influence the choice of relatives of missing persons to type. STR and SNP offer high powers of discrimination, the latter if array technologies are used. ADS will be exemplified by analysis of first and second pedigree examples such that an algorithm for ADS results.

Referring first to FIG. 1, there is shown a first pedigree example. The missing person or victim is indicated with a shaded box where a box represents a male and a circle a female. For example only, it is assumed in FIG. 1 that the missing person 2 is male and that an unknown specimen that may have originated from missing person 2 has been typed using all three DNA typing technologies. A diagonal line represents that the missing person 2 or other relative shown in the pedigree diagram is deceased or DNA is otherwise unavailable. The horizontal line connecting sibling 8 and sibling 10 to missing person 2 represents kinship at the same level while the vertical line connecting to parents 14 and 16 indicates the next higher level of kinship and so on. With reference to FIG. 1, missing person 2 is male and married to female 4. Female 6 represents a female child of missing person male 2 and female 4. Parent 14 has a female child 12 by another spouse than spouse 16 who is deceased, indicated by the diagonal line. So child 12 is a half-sister to missing person 2. Unavailable mother 16 has a sister 18, who is missing person 2's aunt. From FIG. 1 (and FIG. 3 using the discriminatory power calculations and graph, for example, of FIG. 2), the following rules of a rule base may be determined.

A very simple rule is utilized as a first-order approach when attempting to identify a person from remains of a missing person. The simple rule is to type (obtain DNA profiles for) both parents if they are available. Typing both parents provides information across all DNA types and an STR profile alone (for example, using the thirteen core loci of the Federal Bureau of Investigation database) provides sufficient discrimination for disasters of moderate size such as an airplane crash. There are corollaries to the general rule. If both parents of the missing person are available and have complete typed profiles, no additional information can be gained from the parents' ancestors or the missing person's siblings, child or spouse. Similarly, if one has complete typed profiles of a child of the missing person, there is no reason to obtain specimens from that child's offspring. Similar properties hold for other relatives, that is, no child provides more information than a parent where the missing person is on the same or higher kinship level than the parent. Referring to FIG. 1, this simple rule of being able to type both parents and so limit the forensic scientist's work is not applicable because only one parent, father 14, is available. A more complicated case where DNA for both parents are unavailable will be discussed in connection with FIG. 3. In FIG. 1, one parent 16, the mother, is not available. For example, mother 16 may also be a victim, for example, in the case of a mass grave or has died with their male child 2 in an airplane crash and is missing as well or otherwise unavailable. Decomposition, confounding influences such as sea or other water and heat or environmental temperature where the specimen is found (typically, weather related), for example, in the case of an airplane crash or fire, degrade DNA. In such situations, it is not realistic to expect complete typing of the STR core loci. If, however, one or both parents' typed profiles are unavailable, or sufficiently degraded, then it becomes necessary to obtain profiles from other relatives, and the correct choice of relatives becomes complex. Consequently, the living male parent, father 14, is selected to be typed indicated by the dots in the square, starting with STR typing, as will be discussed further herein.

In FIG. 1, there is a living female offspring, daughter 6, who may be typed. In the case where only one female offspring, out of all immediate family members, can be typed, it is necessary to look to mother 4, grandparents, aunts 18, uncles, nieces, nephews or grandchildren for further increasing the probability or discriminatory power of a match. Two, three or four individuals may need to be typed in order to obtain a DNA pedigree of sufficiently high discriminatory power for missing person identification. Especially with the availability of multiple DNA typing technologies, for example, STR, Y-STR and mtDNA, the decision of whom to type and which DNA typing technology to use is non-trivial. Even though the mathematics, though convolved, is fairly straightforward and well-known (see, for example, R. C. Elston and J. Stewart. A General Model for the Genetic Analysis of Pedigree Data. *Human Heredity* 21: 523-542 (1971); C. Cannings, E. A. Thompson, and H. H. Skolnick. The Recursive Derivation of Likelihoods on Complex Pedigrees. *Advances in Applied Probability*, Vol 8, No 4. (December 1976), pp 622-625 and E. Lander, and P Green. Construction of Multilocus Genetic Linkage Maps in Humans. *PNAS*, Vol 84, No. 8 (Apr. 15, 1987), pp. 2363-2367), it is not realistic for the average forensic scientist to make a good decision under such circumstances. Consequently, an ADS algorithm and tool as described herein provides an easy-to-use platform for the organization of information about relatives to a missing person, for example, missing person 2 and developing a recommended set of relatives' DNA specimens to type. The ADS algorithm may be run on a portable personal computer. If the ADS tool or portions thereof is implemented on a single personal computer, the portable personal computer may access remote databases and communicate with remote computer hardware via a communications interface and receive input from typing performed on selected relations to missing persons performed remotely. Moreover, the ADS tool is not limited to a personal computer embodiment but may be implemented in firmware, software and hardware on larger or smaller known computer apparatus or plural computer apparatus as will be described further herein in connection with a discussion of FIG. 7.

The rule base and algorithm will now be further defined before completion of the discussion of FIG. 1. Identification of the remains of a disaster victim or missing person MP 2 using DNA evidence is best performed using a Bayesian approach to calculate a Likelihood Ratio (LR) to gauge the relative strength of two hypotheses: (1) there exists a kinship of the stipulated type to known and typed relatives, and (2) there is no relationship between the MP's remains and that of the putative relatives. The relationships between the relatives and the missing person can be captured in a pedigree, to which data that describe specimens, DNA profiles, and metadata can be associated. A fundamental question that affects cost and efficacy of the identification process is the relative discriminatory power of different combinations of family members (measured, for example, by likelihood ratios (LR's), odds, or posterior probabilities). For example, the question may be asked whether the DNA profiles of one parent and one sibling is better able to establish identity than those of two off-springs. For example, the question may be asked whether the combination of a spouse and two off-springs is better than a parent and 2 siblings. Answers to these types of questions require the knowledge of the distributions of the LR of pedigrees having various combinations of family members and the missing person. Such knowledge is best embedded in an automated decision support (ADS) environment due to the complexity of the underlying mathematics. The problem, for example, is studied in FIG. 2, whose underlying mathematical calculations for different combinations of available family members and results may be embedded in the automated decision support algorithm for implementation, as suggested above, as a tool on a personal computer.

Quantitative knowledge of the various likelihood ratio distributions of pedigree families with respect to the missing person, having different combinations of members is required for this automated tool. The tool becomes a computer-implemented method to decide which minimum combination is sufficient to identify remains with high confidence. A threshold pedigree LR value or sliding value, for example, may be based on the confidence in the typing results of a missing person 2 whose DNA may be degraded. The threshold may be established from the distribution for each combination type of pedigree family members that can be used to evaluate the LR that the DNA profile of remains must satisfy to meet desired error criteria. The incremental value of an additional family member, if brought into the pedigree, in aiding the identification can also be established, a priori, before his/her sample is acquired. Identification by pedigree likelihood ratio based on STR DNA can be further strengthened by the use of mtDNA and/or Y-STR DNA. If a disaster victim's (DV's) remains are badly degraded or fragmented, then the use of mtDNA and/or Y-STR DNA, depending on the gender, becomes necessary in matching to a suitably linked family member. Even when the remains are not degraded, the use of mtDNA and or Y-STR DNA typing will increase the discriminatory power over that of using STR DNA alone, for example, when selected relatives to a missing person are more distant and the number of available relatives is limited.

To date, pair-wise or parent-offspring trio comparison tools have been used almost exclusively in mass fatality incidents. It is generally accepted that, except for parent-offspring comparisons, a significant number of fortuitous and false positive matches can occur in pair-wise comparisons based upon either allele sharing or LRs, resulting in weak leads requiring laborious forensic analyst follow up. Parents-offspring trios require that two of the three trio members be known, a rather restrictive requirement. When genetic data are available for multiple pedigree members, pair-wise comparison is ineffective and wasteful. Exclusions can be made using two typed family members that pair-wise comparisons will not detect; further, LR based on multiple family members is predictably much more discriminatory than pair-wise LR in identifying a missing person. Some commercial software exists to perform an analysis for identification of family relationship in paternity, immigration, or inheritance disputes based on one or more typed family members, but not to provide guidance on selection of relatives for genetic typing. The present automated decision support algorithm may compute the pedigree LR of an arbitrarily specified pedigree mix and profiles.

Referring again to FIG. 1, a single parent example is presented. Referring to FIG. 3, an example where both parents are unavailable is manually analyzed to demonstrate the potential benefit and the technical soundness of ADS and to continue the development of a rule base for the ADS tool. The ADS tool implemented, for example, on a personal computer will automate the manual process that is discussed below and requires no undue experimentation for one of ordinary skill in the art to implement. One innovation is the utilization of computed distributions of pedigree LRs to recommend the acquisition of the data most valuable in the identification process.

As already introduced above, FIG. 1 shows an example pedigree of the family of a missing person 2. Remains of the missing person 2 have been recovered; the question is whether these remains correspond to the presumed identity of the missing person 2. The missing person 2 is male, has a spouse 4 and child 6, a brother 10 and sister 8, a half-sister 12, a father 14, and a maternal aunt 18. The mother 16 is deceased, and no DNA samples of mother 16 are available. A sample of the remains of missing person 2 has been typed using all three technologies (STR, mtDNA, and Y-STR), but the remains are degraded so only partial profiles are available for each technology. The degree of degradation being high, it is determined that STR, Y-STR and mtDNA test data be obtained and stored, for example, in a personal computer for the missing person 2 remains. As will be further described herein, non-DNA forensic data may also be stored to improve the probability of a match if such data are known for missing person 2. The question answered by an automated decision support (ADS) algorithm is which DNA samples from relatives should be collected and what typing should be performed, selected, for example, the three well known technologies.

Turning first to SIR data, both the child 6 and the father 14 share one allele at each locus with the male missing person 2. The spouse's 4 SIR profile, together with the child's 6, can be used to identify, for some loci, alleles that the victim or missing person 2 must have (but which may not be present in a profile because of the degraded condition of the remains of missing person 2). Therefore, the SIR profiles of the child 6, spouse 4, and father 14 should be obtained, indicated by the depicted closed circle. Failing this, knowledge of the STR profiles of the siblings 8, 10 is next most valuable. Since the sister 8 is missing a Y chromosome, the brother 10 is preferred over the sister.

Figure 2:
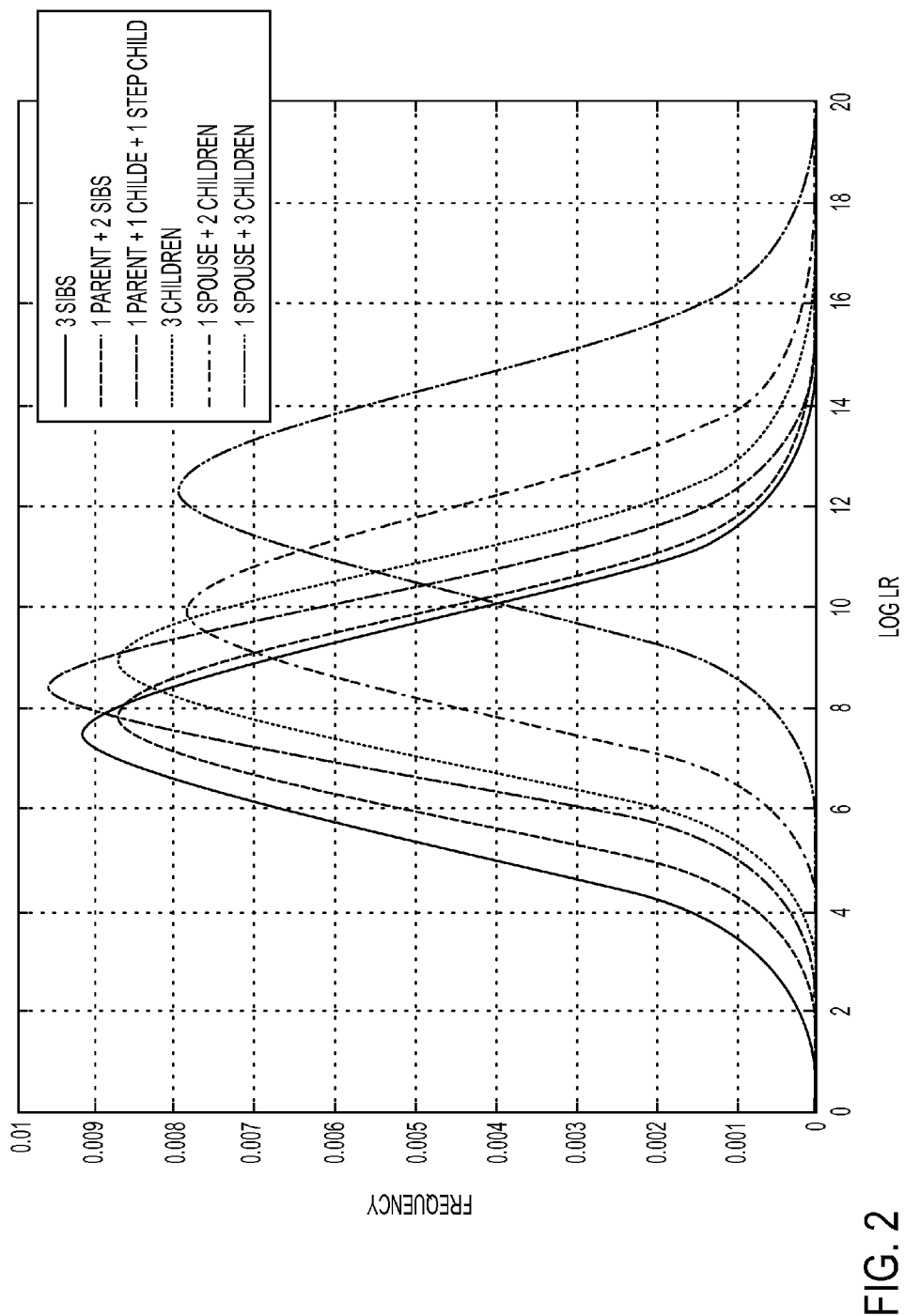
FIG. 2 is a graph of the relative discriminatory power of a pedigree from a left-most logarithmic graph representing a low power level of three siblings in comparison to, for example, a right-most logarithmic graph showing a higher power level for one spouse and three children.

FIG. 2 shows an example of the relative discriminating power of pedigrees having three family members of various relations. The combination of three siblings of a missing family member is the least powerful in this example, with the combination of a parent and two siblings being better. Then follows, a parent and a child, three children, one spouse and two children and the best combination in the example is one spouse and three children. As a second example, Table 1, below provides a list, rank ordered from most to least, of the relative contributions of information for various combinations of typed near relatives which may be stored in computer memory.

TABLE 1

Relative contribution of information (from most to least) to identification of a missing person's remains using STR technology by various combinations of typed near relatives.

1. Both Parents
2. Two Children + Spouse
3. One Child + One Parent + Spouse
4. Two Children
5. One Full Sibling + One Child
6. One Child + Spouse
7. *Two Full Siblings
8. One Parent/Child
9. *One Full Sibling

*Note that a parent or a child in a pedigree acts as a filter to eliminate infeasible candidates, whereas siblings (without parent information) do not.

Continuing with the analysis of FIG. 1, a Y-STR profile, indicated as an "X," can be obtained from either the father 14 or the brother 10. These have almost equal value, with the brother's 10 profile slightly less valuable. The reason the brother's 10 is less valuable than the father 14 is the possibility of mutations, which occur during meiosis. One meiosis event separates the father 14 and missing person 2, while two events separate siblings such as brother 10 from missing person 2. There are no other available male relatives in the example of FIG. 1.

The missing person's 2 mtDNA profile is the same, barring mutations, as those of his siblings 8, 10, his mother 16 (who is unavailable), and his maternal aunt 18. Since the mother is not available and a relevant Y-STR profile can be obtained from his brother 10, it makes sense to obtain a sample from the brother 10 and determine Y-STR and mtDNA profiles along with the STR profile. The sister's 8 DNA is relatively less valuable because she does not have a Y chromosome. Failing this, the aunt's 18 mtDNA can be typed. Mutations are again a consideration when comparing two genetically linked mtDNA or Y-STR profiles where the aunt is removed in kinship from the missing person.

A symbol for each individual is marked in FIG. 1 to indicate the genetic material that should be typed. Thus, the result of a manual analysis of whom to type and how are presented. The sister's 8 DNA could be typed if the brother 10 is unavailable and can in any case provide additional information about the MP's STR profile. Likewise, the half sister 12 and aunt 18 can provide STR data, but the relevant information content is significantly less than information provided by the siblings 8, 10 DNA.

A pedigree likelihood ratio can be computed for each DNA typing technology using the typed genetic data from the chosen family members 4, 6, 10, 14 and 18, comparing the probability that the remains of missing person 2 correspond to the missing person's location in the pedigree (hypothesis 1 above) to the probability that the remains correspond to an unrelated person (hypothesis 2). Computational methods are known in the art. These methods are adapted in ADS to calculate the pedigree LR for arbitrary pedigrees. Since the profile information obtained from each different DNA typing technology can be assumed independent of information from the other typing technologies, a joint likelihood ratio (JLR) can be computed as the product of the likelihood ratios (LR) for each typing technology. A large value indicates the likelihood that the remains correspond to the missing person 2 (hypothesis 1).

The missing person case represented by the second example pedigree, shown in FIG. 3, is more challenging because DNA is not available from either parent, father 24 or mother 26, of missing person 22. (DNA typing of the remains of missing person 22 has been taken using all three technologies as per FIG. 1.) The missing person 22 has a living sister 30, who has children 32, 34 (a boy 34 and a girl 32), a half-brother 28 on his mother's side, and a half-brother 38 and half-sister 36 on his father's side. Aunts 40, 42 and an uncle 44 are also living.

A sample from the sibling sister 30 can provide both STR and mtDNA profiles, but not Y-STR. If the sister's 30 profiles are available, her children's 32, 34 DNA profiles add no new information according to the rule defined above in discussion of FIG. 1. STR information about the parents' genomes can be obtained from the half-brothers 28, 38 (mother's and father's sides) and half sister 36 (father's side only), and from aunts 40, 42 on both sides and the mother's brother 44. DNA profile data for most of these relatives should be used because all of the relationships between the missing person 2 and living individuals are less direct and therefore provide poorer discrimination than was seen in the first example. STR typing is shown for all selected relatives 28, 30, 36, 38, 40, 42 and 44. Typing by mtDNA is shown for relatives 28, 30, 42 and 44, that is, any of the mother's available relatives. Y-STR typing is shown for only half-brother 38 because he has a Y chromosome from his father's side, missing from half-sisters and more relevant than half-brother 28 on his mother's side. As in the first example of FIG. 1, the possibility of mutations should be considered, but, in this example of FIG. 3, the number of meiosis events between the missing person 22 and his living relatives, except for the sister's children 32, 34, is the same in all cases. The symbol for each individual is marked in FIG. 3 to indicate the presence of genetic material that should be typed and how. As before, a pedigree likelihood ratio (PLR), and comparing the probability that the remains of the missing person 22 correspond to the missing person's location in the pedigree to the probability that the remains correspond to an unrelated person, can be computed for each technology using existing techniques and, if desired, combined to generate joint likelihood ratios. Again, the hypothesis tested is whether the missing person 22 whose remains have been found is more probably than not related to the available family members of FIG. 3.

Methods of Predicting Whether an Unknown Specimen is Related by Kinship

Figure 5:
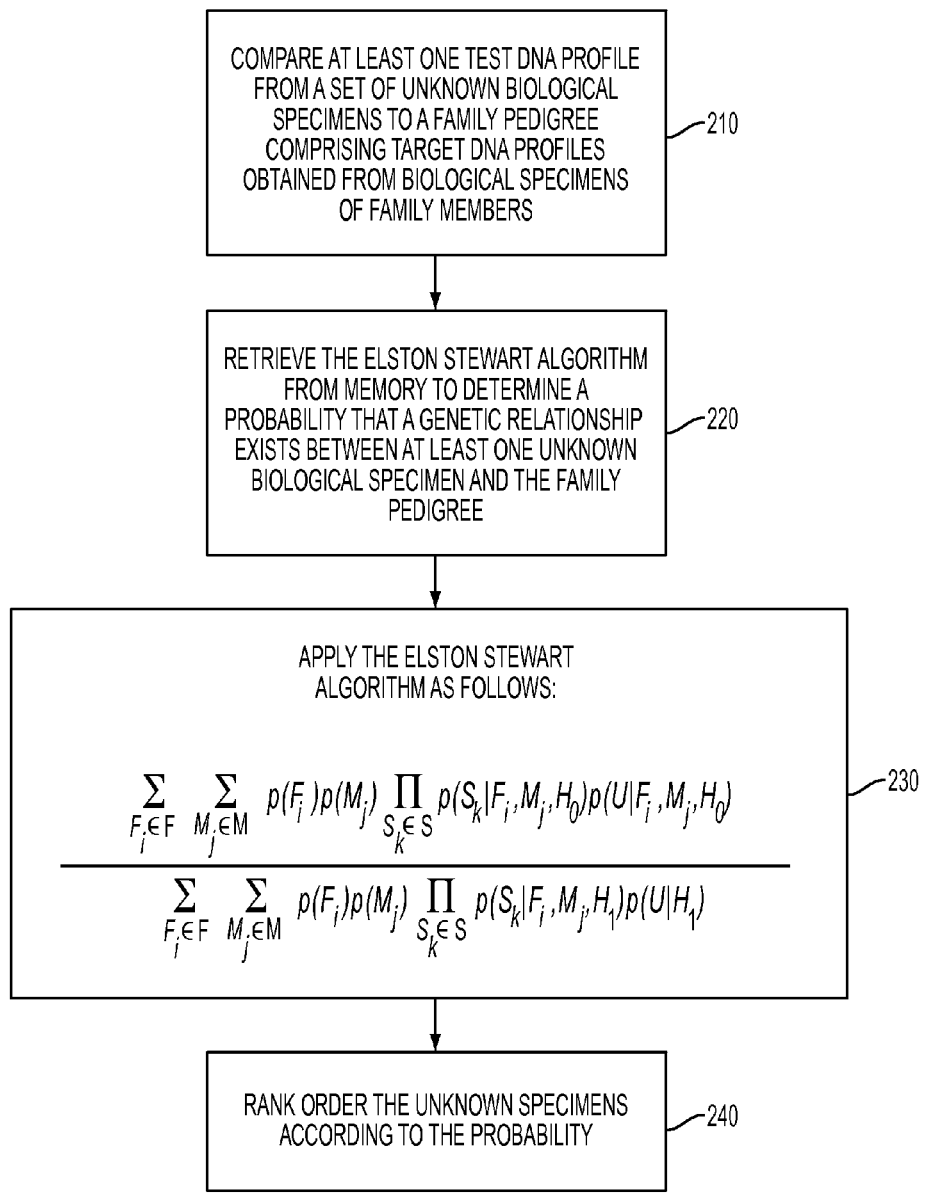
FIG. 5 is a flow diagram that illustrates an overview of one embodiment of a method of identifying an unknown biological specimen as likely related to a family pedigree comprising at least a first and second family member.
Figure 6:
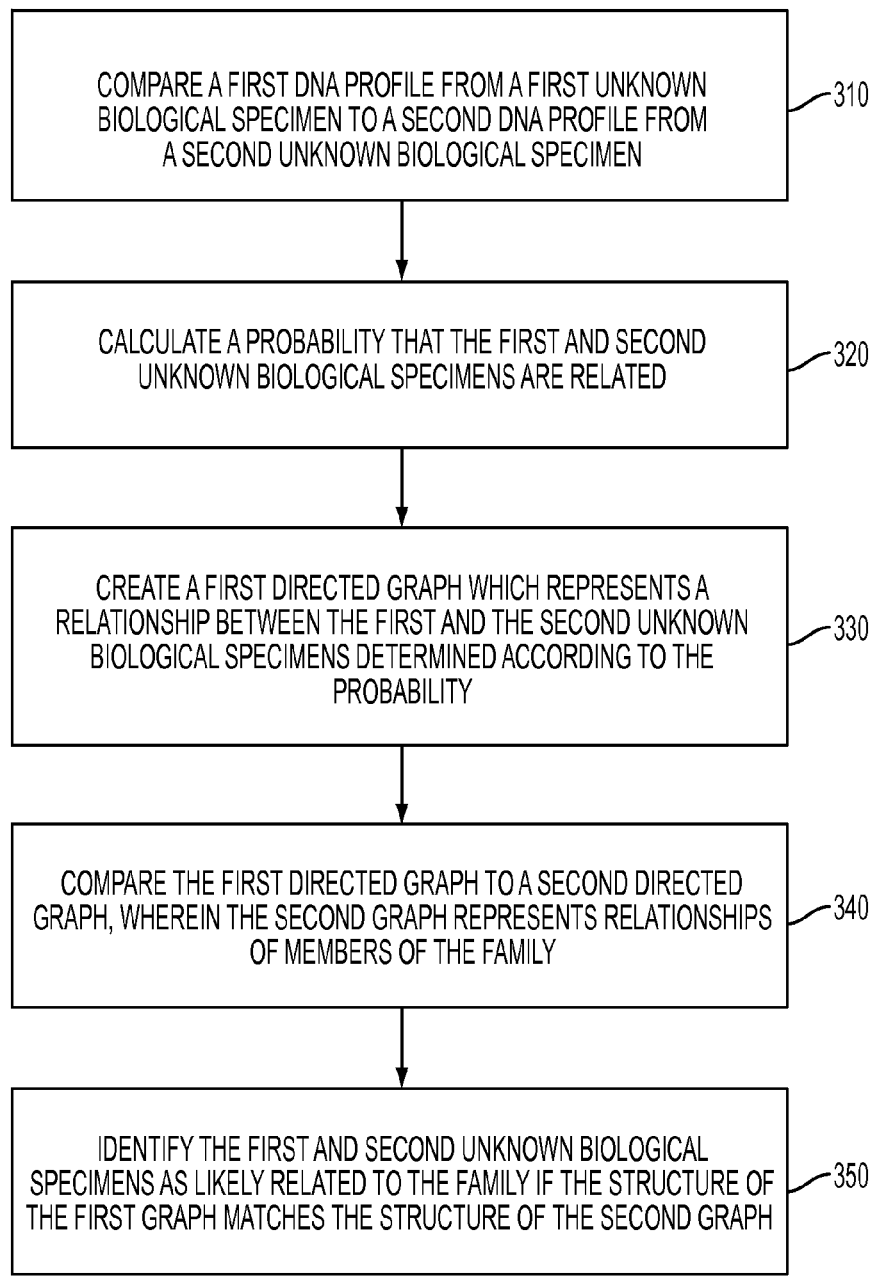
FIG. 6 is a flow diagram that illustrates an overview of one embodiment of a method of identifying at least two biological specimens as likely related to a family comprising at least a first and second family member.
Figure 7:
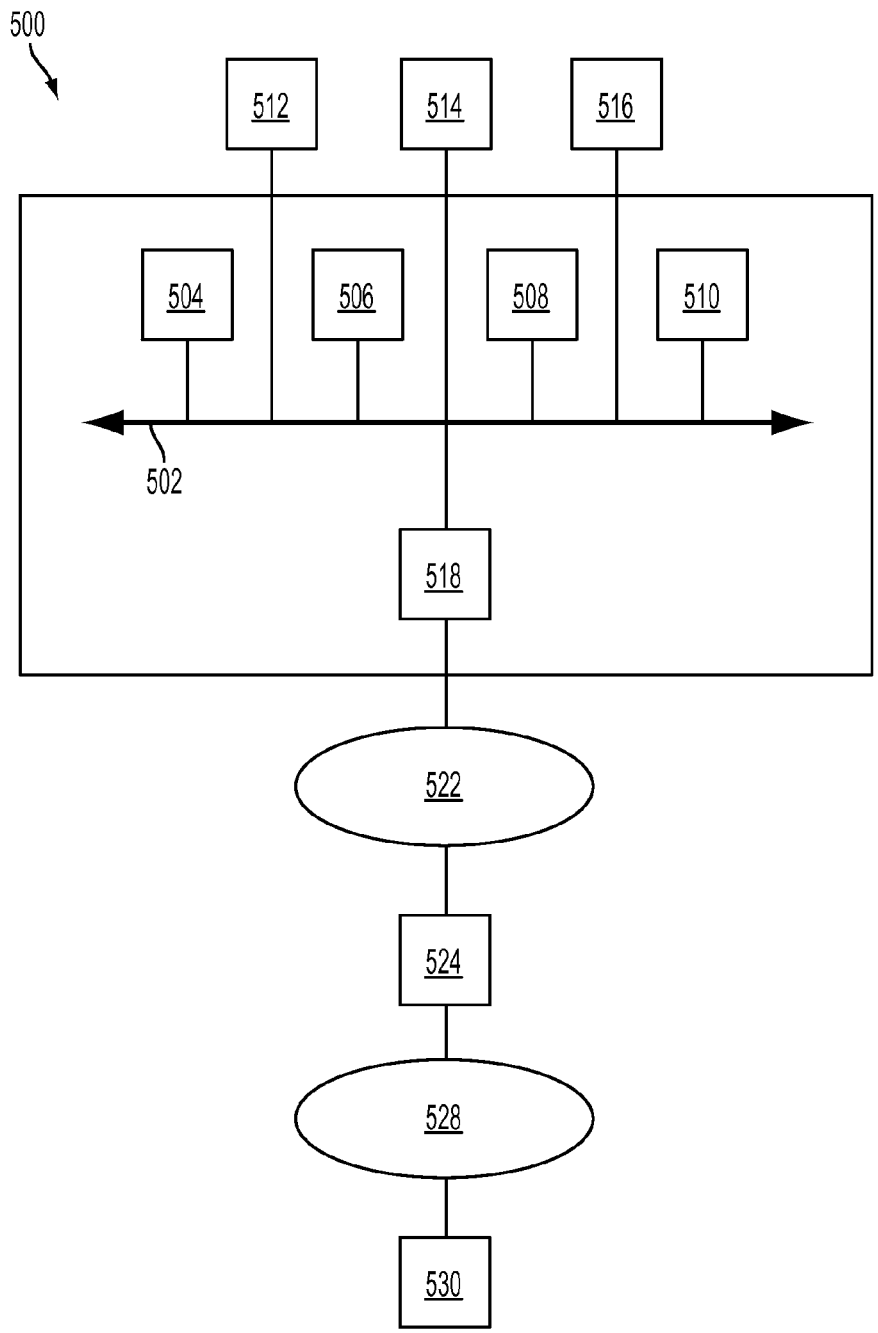
FIG. 7 illustrates a block diagram of a hardware environment that may be used according to an illustrative embodiment of the invention. Now the various embodiments will be described with reference to the drawings.

Referring to FIGS. 5-7, there will now be described several embodiments of methods of predicting whether an unknown biological specimen from an individual originates from a member of a particular family. The individual can be deceased or can be living but unidentified. Methods of an embodiment may use as much available DNA profile information as possible but may be reasonably limited as discussed above with respect to automated decision support (ADS). The methods permit a forensic investigator to identify an unknown biological specimen by ranking test DNA profiles from unknown biological specimens according to calculated probability, likelihood, likelihood ratio, or a likelihood function values that the test DNA profiles are related to target DNA profiles from family members of the missing individual. If an unknown biological specimen has high likelihood function values when compared to more than one target family member, this can indicate an increased likelihood (or probability) of a relationship between the unknown biological specimen and the family.

Prediction methods typically are used with humans but can also be used for any type of individuals that can be grouped into a family. A "family" according to the invention is a group of individuals who are genetically related to a missing individual. A mother, father, grandfather, grandmother, full or half siblings are examples of members of a family, as are cousins, aunts, and nephews, half-brothers and half-sisters and so on. The corresponding missing individual is also a member of the family (the hypothesis to be demonstrated). Genetic relationships exist within a family according to the Mendelian laws of inheritance. When one calculates a likelihood or likelihood ratio (LR), one takes into account known or stipulated genetic relationships such as parent-child, siblings, etc. For example, half of the genetic information contained in a father's nuclear DNA (other than the Y chromosome) will be inherited by a child. Only ¼ of the genetic information contained in a grandfather's nuclear DNA (other than the Y chromosome) will be inherited by his grandchild. All of a mother's mitochondrial DNA (mtDNA) will be inherited by her child. All of a father's nuclear DNA from the Y chromosome will be inherited only by his son. The inheritance of both nuclear and mitochondrial DNA may be influenced by mutations as suggested above. The present prediction methods exploit these genetic relationships to identify an unknown biological specimen as having a probable or likely genetic relationship to the typed genotypes of members of a family.

Suitable families include those of vertebrates, most particularly mammals, including primates (e.g., gorillas, chimpanzees, baboons, squirrel monkeys, humans), companion animals (e.g., cats, rabbits, dogs, horses), farm animals (e.g., cows, sheep, swine, goats, horses), wild animals (e.g., lions, tigers, elephants), and research animals (e.g., cats, dogs, guinea pigs, rabbits, sheep, goats, swine, chimpanzees, mice, rats, and baboons). However, the methods are not limited to species of vertebrates and may be used whenever Mendelian laws of inheritance are known. For example, the methods may be used for families of a plant or other animal species.

The methods' power is based in part on comparison of DNA profiles from unknown biological specimens to DNA profiles of more than one family member, which significantly increases the methods' predictive ability. A "DNA profile" according to the embodiments comprises one or more DNA markers which together uniquely characterize(s) an individual with high probability and which contain inherited genetic information. A DNA profile can be from one or more of the following DNA types, which correspond to both the source of the DNA and the laboratory process used to obtain the information: single nucleotide polymorphism (SNP), autosomal short tandem repeat (STR), mitochondrial DNA (mtDNA), mini-SIR, or STR DNA from the Y chromosome (Y-STR). In the future, additional DNA types will most likely be developed, and since the methods disclosed herein rely upon the Mendelian laws of inheritance and the mathematics of probability rather than a specific DNA typing technology, these methods will also apply to any newly discovered DNA types. A DNA profile typically contains one or more DNA markers (e.g. 1, 2, 3, 4, 5, 6, 7, 8, 9, 10, 11, 12, 13, 14, 15, or more), which can be of various types. For example, polymorphic STR loci which can be included in a DNA profile include D3S1358, vWA, FGA, D8S1179, D21S11, D18S51, D5S818, D13S317, D7S820, D16S539, THO1, TPOX, CSF1PO, Penta D, Penta E, and D19S433.

DNA profiles for use in predictive methods of the embodiments are obtained from biological specimens. A "test DNA profile" according to the embodiments is a DNA profile obtained from an unknown biological specimen or an individual with a questioned relationship, such as missing person 2 of FIG. 1 and missing person 22 of FIG. 3. A "target DNA profile" as defined herein is a DNA profile obtained from a biological specimen of a personal effect of a missing person or a known family member. A "biological specimen" as defined herein is a sample from which DNA can be obtained. Suitable samples include, but are not limited to, nucleated blood cells, bones or bone fragments, skin cells, hair, saliva, cells obtained from a cheek swab, and DNA remaining on a personal effect, such as a toothbrush, bedding, a razor, a glass used for drinking, a cigarette butt, or a hairbrush. An unknown biological specimen can be derived from living tissue (e.g., a biopsy) or from deceased tissue (e.g., remains), bone fragments, hair, or fingernail scrapings.

One can extract DNA from an unknown biological specimen by using any DNA extraction technique. Many techniques for extracting DNA are well known in the art. See, for example, Gurvitz et al. *Australas. Biotechnol.* 1994 March-April; 4(2):88-91; Ma et al. *J Forensic Sci. Soc,* 1994 October-December; 34(4):231-5; Laber et al. *J Forensic. Sci.* 1992 March; 37(2):404-24. Methods of obtaining DNA profiles from the extracted DNA are well known in the art and include, but are not limited to, DNA sequencing, restriction digestion, polymerase chain reaction followed by electrophoresis, and microarray analysis.

Referring to FIG. 5, in one embodiment, an unknown biological specimen is identified as likely related to a family of at least two family members by its position in a rank-ordered "combined list." The combined list 140 comprises two or more family member lists, for example, obtained from relatives of missing persons. A "family member list" 130 comprises a set of unknown biological specimens rank-ordered according to a calculated likelihood function value that a genetic relationship of a specific type exists between test DNA profiles obtained from the set of unknown biological specimens and a target DNA profile obtained from a biological specimen of a family member. The combined list 140 comprises the set of unknown biological specimens rank-ordered according to a calculated probability/likelihood that a genetic relationship exists between test DNA profiles and target DNA profiles from at least two family members. A highly ranked unknown biological specimen is identified as likely related to the family at 150.

One embodiment of the present invention involves searching at least one database containing test DNA profiles derived from unknown biological specimens (for example, comprising disaster victims) and comparing these profiles to target DNA profiles from known family members (surviving family members of disaster victims). Test DNA profiles may all be of one type (e.g., a set of short tandem repeats; STR DNA) or there may be multiple types of test DNA profiles for one or more samples. Test DNA profiles can be stored in a database according to profile type (DNA typing technology), or a single database may store DNA profiles having information about multiple DNA profile types. For example. STR test DNA profiles may be stored in a STR test DNA profile database; mitochondrial test DNA (mtDNA) profiles may be stored in a corresponding mitochondrial test DNA profile database and Y-STR results stored in a corresponding database and so on.

Figure 4:
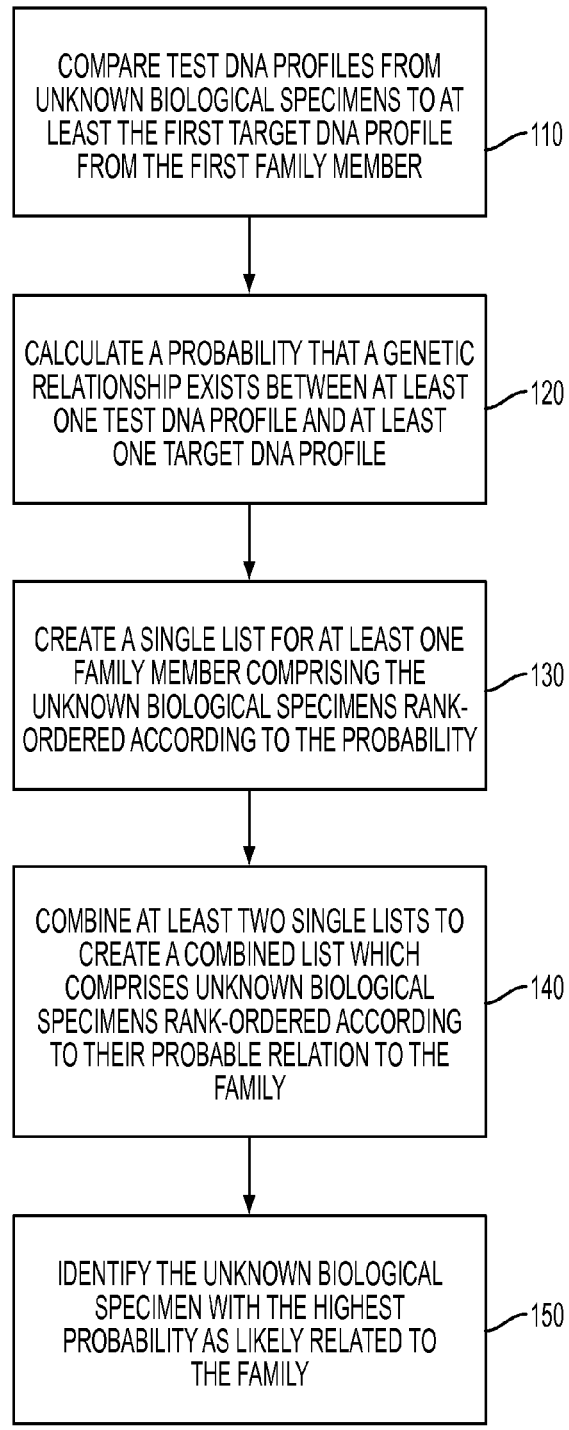
FIG. 4 is a flow diagram that illustrates an overview of one embodiment of a method of identifying an unknown biological specimen as likely related to a family comprising at least a first and second family member.

Referring again to FIG. 4, in block 110, the DNA profile comparison can be made manually but implementation on a computer, such as a personal computer, is preferred. Thus, as will be further described with reference to FIG. 7, a database preferably contains a search engine, for example, processor 504, which implements search, match, and retrieval methods for a particular test DNA profile type. Search engines preferably are both efficient and scale sublinearly (e.g. logarithmically) with database size.

In block 120, a probability or likelihood that a genetic relationship exists can be determined by a variety of methods. The likelihood that a relationship exists between a test DNA profile from an unknown biological specimen and a target DNA profile from a family member can be evaluated mathematically. For example, an unknown profile cannot be excluded as a child of a DNA typed parent if the unknown biological sample has at least one STR allele in common with the parent at each locus. For other family members, one uses likelihood ratios (LR's discussed above) or a likelihood function for this determination, but other evaluation methods can be used, such as expert systems or heuristic rules. An exemplary expert system is described by U.S. Pat. Nos. 7,624,087 and 7,640,223. A probability, in this sense, is defined as the mathematical chance that a given genetic profile is observed for the test profile conditioned on the genetic profiles observed for the family relatives under the hypothetical biological relationship between missing person and family. Note that the hypothetical relationship may be in the usual sense of a relationship between two members of a family, or it may be the hypothesis that a relationship does not exist or cannot be determined (hypothesis 2). Probability is expressed as a number between zero and one. Zero means that it is impossible to observe the test profile under the hypothetical relationship, and one implies that the test profile would be observed with certainty under the hypothetical relationship and the observed profile of the family member(s). A likelihood is defined as the reciprocal of a probability, A "likelihood ratio" or LR is defined as a ratio of two probabilities. The probability of the observation of a set of profiles under the assumption that the specimens are related divided by the probability of the same set of profiles under the assumption that the specimens are not related would be one example of a likelihood ratio. The relationship may be between two specimens, or between a specimen and specimens associated by members of a family pedigree, possibly including missing persons. In any of these embodiments, a probability may be replaced by another measure of the possibility or likelihood, or a likelihood function of a relationship. A "likelihood function" may be defined herein to comprise any probability, likelihood, or likelihood ratio calculation that evaluates the degree of manifestation of a genetic relationship between at least two DNA profiles, biological specimens, graphs, or possibly anything which represents an individual or a family.

"Filtering", as defined in these embodiments, is the exclusion of specimen, or DNA profiles that are not compatible with a family pedigree, or possibly additional information, based upon either DNA or non-DNA information. A "family pedigree" comprises information about the members of a family, where the family may include biological specimens, individuals, or missing persons and the information can be DNA information or non-DNA information, and information, either explicit or implicit, that describes the relationships among the members of a family. Filtering or excluding also refers to narrowing or limiting potential search results. It is desirable to perform such filtering using efficient database search methods. The methods of organizing data into clusters, indexed storage and retrieval of multidimensional information and partitioning data records described in U.S. Pat. Nos. 6,741,983; 7,242,612 and 7,454,411 and pending related applications are suitable for DNA information clustering. Efficient database search methods are well-known for non-DNA information. A database may be parallelized in order to enhance performance and/or scalability, as described in U.S. Pat. No. 7,454,411.

For example, if in a family pedigree comprising a father, mother, and two children, typed STR DNA is available for the father, and a child is missing, a search of a database of unidentified human remains can be performed to return all specimens having DNA profiles that are compatible with the father's STR DNA profile. In this case, STR DNA profiles are classified as compatible when at least one allele is shared by the father and child at each STR DNA locus, except for loci of the Y chromosome, in which case all Y-STR DNA alleles are shared if the child is male. If, for example, within a family pedigree, mtDNA is available for a mother or a relative sharing the same maternal lineage, then a search could be performed to return all specimen having mtDNA profiles that match the mtDNA of the typed mother or the maternally linked relative. Additionally, non-DNA forensic information can be used, for example, to exclude samples from remains found before the last date and time the child was seen. The benefit of using a search to filter or exclude specimens is that one has the ability to use an efficient database search method to rapidly prune the size of the population of specimens that must be further analyzed and ranked using, for example, a likelihood function, which may be less efficient than a database search.

Once the probabilities or likelihoods of genetic relationships between unknown biological specimens and family members are evaluated, the unknown biological specimens are rank-ordered according to the likelihood value of being related to a family member. Referring again to FIG. 4, a family member list 130 can be created for at least one family member. The family member list created in block 130 may contain unknown biological specimens listed in order of their likely relationship to the family member. At least two single lists from different family members are then combined into one combined list 140. For example, family member lists from a mother, father, or grandfather can be combined into one combined list 140 which represents the list for the family. Lists can be combined by summing, averaging, or using other mathematical operations to merge data from at least two lists into one combined list. Such combining can be accomplished by performing mathematical operations on the likelihood function values used to order the biological specimens of each list, by performing mathematical operations on the positions or relative positions of the biological specimens of each list, or by a combination of these methods. It can be desirable to exclude an unknown biological specimen from a combined list if the specimen can be excluded from one of the family member lists. It can also be desirable to exclude unknown biological specimen from a list if the specimen has been identified. In block 150, the top few highest-ranked unknown biological specimens in the combined list contain the unknown biological specimen that is most likely the correct missing person for this family. More generally, the unknown biological specimen that corresponds to a specified missing person is likely to be highly ranked.

In another embodiment, referring to FIG. 5, when multiple genetically related family members are available to donate their DNA, the DNA should be used jointly and simultaneously, for example, according to automated decision support described above, to derive a joint likelihood ratio (JLR), or pedigree likelihood ratio (PLR). This PLR between the missing person/victim and the family pedigree is derived under the hypothesis 1 that the missing person is related in the stipulated manner to the family pedigree, against the hypothesis that he/she is unrelated to the family pedigree (hypothesis 2). For a family pedigree under consideration, the PLR for each potential missing person candidate is to be calculated, and the missing person candidates are then ranked according to the PLR. The top ranked candidates should contain the correct missing person sought after by the family corresponding to this family pedigree. Mathematically, the more members of a family pedigree that are available and typed according to automated decision support discussed above or the closer they are related to the missing person, the more precise and effective the ranking will be. PLR is based on the set of available genotype information of the multiple family members, explicitly incorporating into its calculation the known relationships among the family members and the putative relationship to the missing person candidate.

In this embodiment, referring to FIG. 5, relationships between multiple known target DNA profiles from a family which are described by a family pedigree are used to evaluate the likelihood that the unknown specimen is from the missing person related to the family (hypothesis 1). In this embodiment, in block 210, a test DNA profile from at least one unknown biological specimen is compared to the genetic information of the family pedigree which comprises target DNA profiles obtained from biological specimens of at least two family members. As explained above, an ideal family pedigree exists when DNA typing of both parents of a missing person is available. The comparison can be made manually or, preferably, the comparison is implemented in the form of an algorithm installed on a computer. In block 220, a modified Elston Stewart algorithm can be retrieved from computer memory 506, 508, 510 as shown in FIG. 7 for calculating a pedigree likelihood ratio that a genetic relationship exists between at least one unknown biological specimen and the members of the family pedigree. In block 230, a modified Elston Stewart algorithm accomplishes this mathematical evaluation by providing a pedigree likelihood ratio that a test DNA profile from an unknown biological specimen has a genetic relationship of a specific type to a family pedigree.

The original Elston Stewart algorithm (R. Elston, J. Stewart, "A general model for the genetic analysis of pedigree data." *Hum Hered.* 21 (1971) 523-542), incorporated by reference herein as to any information deemed essential to an understanding of the embodiments includes a penetrance term expressing the probability of phenotypic expression of a disease if the individual bears the genotypic disease marker. It also includes a probability measure for the degree of linkage of markers residing at different loci. The Elston and Stewart algorithm was adapted to use the penetrance term instead to represent the probability of mutation at an allele that occurs during meiosis from a parent to child lineage inheritance event, if occurrence of mutation is to be considered. If mutation occurrence is not to be considered, then the penetrance term is set to 1. In addition, the term that expresses a linked relationship between markers residing at different genetic loci is not used. The original algorithm is adapted to accommodate the assumption of independence of marker alleles residing at different loci, although should an assumption of independence of marker alleles not be valid for some future DNA type adopted by the forensics community, the term that expresses a linked relationship can be re-inserted in the algorithm. An example mathematical equation for this pedigree likelihood ratio (PLR), without considering mutational occurrence, for a family pedigree comprised of a father, mother, and sibling(s), where either the father, mother, or both can be genetically un-typed is $$PLR = \frac{\sum_{F_i \in F} \sum_{M_j \in M} p(F_i) p(M_j) \prod_{S_k \in S} p(S_k | F_i, M_j, H_0) p(U | F_i, M_j, H_0)}{\sum_{F_i \in F} \sum_{M_j \in M} p(F_i) p(M_j) \prod_{S_k \in S} p(S_k | F_i, M_j, H_1) p(U | H_1)}$$

where F and M are the sets of possible DNA profiles for the father and mother, respectively, S is the set of DNA profiles for typed siblings, and U is the DNA profile for the unidentified human remain. $H_0$ is the hypothesis that the unidentified human remain is front a missing child in this family pedigree, and $H_1$ is the hypothesis that there is no known relationship between the unidentified human remain and the family pedigree. This equation is one example PLR for this family pedigree. Equations for family pedigrees comprised of different combinations of family members can be written using the same adaptation to the Elston Stewart algorithm or similar published works, such as those by E. Lander and P. Green (Lander and Green 1987) or by C. Cannings, E. Thompson, and E. Skolnick (Cannings et al. 1976) and others (Dudbridge F. 2003; Fernandez et al. 2001).

A PLR can be evaluated in different ways. For example, a straightforward way to evaluate the above equation is to enumerate all possible unknown profiles and multiply and sum over these enumerated unknown profiles the probabilities and conditional probabilities that depend upon them. Simplifications can be used, as indicated above, when the profile of either the father or the mother, or both, is known. Many loci are independent from each other, and in this case a term can be calculated for each independent locus, and the product of these terms can then be incorporated in the PLR. Another way is to consider the number of alleles or genotypes that are inherited by a child from one or both parents and use a probability or conditional probability that this number has occurred. This is known as "identical by descent" (IBD), and in this case the terms of the PLR are grouped according to the number of alleles or genotypes IBD. A calculation using an IBD approach can consider 113D alleles between any two genetically related biological specimens or individuals; it is not restricted to parent/child relationships. Alternatively, portions of the equation for the PLR may be pre-computed. This can be especially beneficial when the PLR is to be calculated for a number of unknown human remains; for example, the product terms over all known siblings may be pre-computed. Another way is to predetermine a sequence of machine instructions that can be executed to calculate the PLR for a given family pedigree in a highly efficient manner, and then execute these instructions for each of a set of unknown human remains. Finally, if the family pedigree incorporates multiple generations, the PLR may be computed in a recursive manner, in either a bottom-up or top-down fashion. The family pedigree may contain loops, in which case the approach of C. Cannings, E. Thompson, and E. Skolnick, or a similar approach, may be employed.

Pedigree likelihood ratios, as described above, can be used to evaluate whether there is a reasonable degree of certainty that an identification determined in this manner is correct. Optionally, as shown in block 240, the unknown biological specimens can be rank-ordered according to a pedigree likelihood ratio that at least one unknown biological specimen is related to the family or family pedigree. Higher-ranked unknown biological specimens are more likely to be candidates for the correct missing family member sought by the family represented by the family pedigree.

Another embodiment of the invention, referring to FIG. 6, takes advantage of known or hypothetical relationships between biological specimens. This embodiment is particularly suitable to large-scale mass disaster or terrorist incidents where several related members of families are missing or among the victims, such as occur in airplane crash disasters and natural disasters such as volcano eruptions or tsunamis. A database of DNA profile data from both known and unknown biological specimens can have hypothetical relationships between specimens, some of which may be known to be true, for example, samples taken from various portions of an unidentified remain, and samples from known or related sources. Hypothetical relationships may be based upon, for example, additional forensic evidence linking unidentified remains. Hypothetical relationships can also be tested using standard methods such as likelihood functions, maximum likelihood identification, or maximum likelihood estimation that provide a quantitative measure of the potential validity of each hypothesis. Discovered relationships are hypothetical relationships having a high degree of correctness, and may be based upon, for example, non-DNA forensic information (see below) or mathematical analysis such as the use of likelihood functions or maximum likelihood identification and a decision process whereby a hypothesis of relatedness is accepted and recorded or discarded. One possible decision process is comparison of the value of a likelihood function to a numeric threshold and acceptance if the value is greater than the threshold.

Referring again to FIG. 6, to determine whether a relationship may exist between two biological specimens (known or unknown), block 310, a DNA profile from one biological specimen is compared to a DNA profile from another biological specimen to determine the probability or likelihood that a genetic relationship exists. Such a relationship can be called a hypothetical relationship. The comparison can be carried out by calculation of the value of a likelihood function and comparison of the value to a threshold. A second approach is to use maximum likelihood estimation or to compute the joint conditional probability of occurrence of the two DNA profiles for a set of hypothetical relationships, and accepting and recording one or more of the relationships having greatest likelihood or probability as having support from the available information. Once two biological specimens are compared, a likelihood of a hypothetical relationship between the two specimens is calculated as described above and shown in block 320. It is important to recognize that multiple hypothetical relationships between two specimens may be accepted for recording, and that each specimen may have accepted relationships with zero, one, or more other specimens. In this context, "accepted for recording" means that the evidence for the relationship, for example, based upon forensic evidence or calculated likelihood, is sufficiently strong to indicate that the possibility of this relationship should be recorded, or maintained, for example, in a database for further evaluation or analysis. Each hypothetical or known relationship between the biological specimens can be represented, or recorded, as an edge of a directed graph 330. The term "recorded" is used in these embodiments to show that a relationship has been represented by an edge of a directed graph. A directed graph, as defined in the field of computer science, contains nodes which correspond to specific data and edges which correspond to relationships among the data. An edge has a direction from one node to another, and this edge can represent a dependence of one node upon another, such as "node A is a child of node B". The term "directed graph" is used here to indicate that such dependencies can be represented; however, other methods of representing such dependencies are known in the art, such as entity-relationship diagrams or relations between records in tables of a relationship database. Therefore, the term "directed graph" is defined to mean any representation of entities or objects, such as are needed to represent biological specimens, DNA profiles, or individuals, and relationships between these entities or objects that are not necessarily reflexive, meaning, for example, that "node A is a child of node B" does not imply that "node B is a child of node A". Information may be associated with any node or edge to more completely describe the data or relationship. In these methods, nodes of the directed graph correspond to individual biological specimens and/or their DNA profiles, and edges of the directed graph correspond to known or hypothetical and accepted genetic relationships between the biological specimens. In block 340, a family pedigree comprising relationships among family members can also be represented as a directed graph.

In this embodiment of FIG. 6, a directed graph that represents a hypothetical or known relationship between biological specimens or individuals and/or the corresponding test DNA profiles is compared to a directed graph that represents a family pedigree defining relationships between individuals (known or missing) at block 340. The objective of the comparison is to identify portions of the directed graph that represent hypothetical or known relationships between biological specimens or individuals and or the corresponding test DNA profiles that at least partially correspond to the structure and information specified by the directed graph that represents a family pedigree. The comparison, as shown in block 340, can involve the structure of the directed graph in addition to the DNA profile information contained in the directed graph. For example, the directed graph that represents a family pedigree may describe parent and child relationships of a family, where many families are missing due to a mass disaster, such as occurred subsequent to the Southeast Asian/Pacific tsunami of 2005. Such a comparison may yield many possible matches, corresponding to multiple missing families. If additional known information is included in the directed graph of the family pedigree and its associated data (such as DNA profiles of known individuals or non-DNA forensic evidence), the search would be more focused and may yield one to only a few possible matches. Comparison may be done manually or, according to a computer-implemented algorithm on a computer system according to FIG. 7. One approach to implementing this method is to build upon existing directed sub-graph matching or (partial) isomorphism search and retrieval methods. A search can identify isomorphic structures in the database corresponding (partially) to a target directed graph, and compare test DNA profile information to determine any candidate matches to target DNA profiles which lie within the defined neighborhoods, as shown in block 350. Multiple test DNA profiles in the database may match simultaneously within a stored directed graph structure, corresponding to multiple test DNA profile types corresponding to an unknown biological specimen and/or the test DNA profiles corresponding to multiple biological specimens associated by a sub-graph that is at least partially isomorphic to the target directed graph, as shown in block 350. A second approach to implementing this method utilizes link discovery methods to discover clusters within the directed graph that is constructed as described herein. These clusters correspond to groups of related specimens and individuals and include the family pedigree information represented within the database. Link discovery methods can also be used to identify and visually inspect clusters of related nodes corresponding to individuals and/or remains.

One way in which this embodiment can be implemented is to construct a database that contains information about specimens and individuals. Note that a "database" may be implemented as a collection of databases or database tables, or it may be any other method of organized information storage. Each specimen or individual can be represented in the database as a node or database object, as this term is known in the literature, corresponding to a node of a directed graph. DNA and non-DNA information about each specimen or individual can be associated with this node using methods that are known in the field of computer science. Known relationships between specimens or individuals can also be stored in the database and correspond to edges of a directed graph containing the nodes. A list of possible relationships between individuals or specimen can be maintained, and the list defines the set of possible hypothetical relationships between specimen or individuals. For any pair of specimens or individuals represented in the database, a likelihood function value of each possible hypothetical relationship can be calculated based upon the information stored in the database, and this likelihood function value can be tested to determine if information about a hypothetical relationship between this pair of specimens or individuals should be stored in the database. If the result of this test determines that the hypothetical relationship should be stored or recorded, the hypothetical relationship can be recorded as an edge in the database with associated information including, for example, the hypothetical relationship and the likelihood that the hypothetical relationship is true. More than one hypothetical relationship may be recorded in this manner for any pair, although in many cases no hypothetical relationship will be recorded because the available information does not support the hypothesis that a relationship exists. In this manner, a database can be constructed that contains DNA and non-DNA information about specimens and individuals and their relationships and includes hypothetical relationships that are evaluated to be sufficiently likely to be true. The terms "likely" and "likelihood" may correspond to the mathematical definitions of likelihood functions or likelihood ratios from the fields of population genetics, statistics, or probability, but this is not necessary. Other functions that quantify the strength of a hypothetical relationship between two individuals or specimens relative to other hypothetical relationships may be used, such as probabilities, log likelihood functions, or measures of genetic similarity such as the number of genetic markers in common, the relative lengths of two genetic sequences, or the edit distance between two genetic sequences.

An advantage of this method over existing methods is its ability to simultaneously hypothesize and record multiple possible relationships. A second advantage is that a specimen may be related to multiple family pedigrees through edges of the directed graph that correspond to accepted and recorded hypotheses. Thus, unlike previous methods, the specimens are not partitioned into disjoint subsets that are hypothetically related to a single family pedigree. Such a partitioning can result in classification errors, since at the partitioning step insufficient information is known to accurately perform the partitioning. An incorrect assignment of a specimen to a partition in this case would eliminate the possibility of correctly identifying the specimen's family pedigree at a later time. In contrast, a method of one embodiment allows a specimen to hypothetically belong to more than one family pedigree, and subsequent mathematical analysis, such as by using a pedigree likelihood ratio, can be used to determine the correct family pedigree.

A family pedigree containing information about individuals and relationships can be used as a target for a query or search of this database to locate portions of the database that are likely to correspond to the structure and information provided by the family pedigree. Such correspondence can be further evaluated using a pedigree likelihood ratio such as a modified Elston Stewart algorithm or other quantitative evaluation of the degree of correspondence of that portion to the family pedigree, relative to other possible portions of the database. In this manner, multiple portions of the database, which can be described as sub-graphs, can be identified as possibly corresponding to the family pedigree, and such portions can be rank ordered using, for example, a pedigree likelihood ratio. Since there may be ambiguity within each portion as to the relationships among individuals and samples, evaluations of multiple possible family pedigrees within this portion can be performed to determine the more likely family pedigrees, providing a method of identification of possible relationships among, for example, unidentified human remains, using methods that are well-known in the field of DNA forensics, similar to those used, for example, to analyze the mass grave containing the probable remains of the Romanov family.

An alternative method is to search first for DNA profiles with likely or probable genetic relationships, followed by a search for matching directed sub-graphs to the target directed graph. Preferably, one would perform these searches simultaneously. One method for implementing this is to alternately resolve searches for potentially related DNA profiles and sub-graph structures at each level of a database index structure, where each level successively reduces the set of possible matches to the target directed graph and DNA profiles within the database.

The process of discovering relationships among biological specimens can lead to the identification of at least two biological specimens with similar DNA profiles, suggesting that these specimens are derived from the same individual. Biological specimens with similar DNA profiles can be collapsed into one specimen to enhance the speed and efficiency of the search.

An advantage of the rapid advances over the past decades in available computational capabilities is that idle computational capability is either available during periods of reduced utilization, or can be made available through the addition of computational elements or partitioning of available computational resources among several tasks. A computer-implemented program running on one or shared among many processors can allocate these unused computational capabilities to background processes that do not have to perform in a time-critical environment. It is advantageous to utilize background processes which may be likewise computer-implemented, also referred to as "spiders," to examine stored data during idle periods, determine hypothetical relationships between samples and their corresponding DNA profiles stored in a database, perform analyses to assess the potential truth of these hypothetical relationships, and record edges in the database indicating the presence of these hypothetical relationships. Such relationships can subsequently form the basis for information that can be compared to target family pedigrees, or directed graphs representing those family pedigrees, and associated DNA profiles in order to achieve identification of unknown remains, associate such remains with missing individuals, and link these items to relatives. Such spiders, or background processes, can thus provide a substantial benefit by improving the accuracy, efficiency, and speed of identification of unknown biological specimens.

Information about unidentified human remains, known individuals, missing persons, and/or family pedigrees can be collected over a substantial period of time, such as several months to a few years. In this case, the method is applied in a continuous or intermittent manner over at least a portion of this period of time. As new information is added, spiders, or background processes, can evaluate hypothetical relationships between the new information and pre-existing information and record edges in the database indicating the presence of these hypothetical relationships. Such newly recorded relationships can subsequently form the basis for information that can be compared to target family pedigrees, or directed graphs, and associated DNA profiles in order to achieve new identification of unknown remains, associate these remains with missing individuals, and link these items to relatives. Both new information and the results of identifications can enable further identification. For example, identification of a second parent or sibling in a family can be used to assist in identification of additional siblings. New information can also lead to the exclusion of some possible identifications. For example, the identification of an unidentified human remain excludes the identification of this remain as originating from a different person.

The methods described by these embodiments can be either static or dynamic. The method is static if the method is applied at one time to a collection of information that has been gathered about two or more biological specimens from unknown remains, known individuals, and/or missing persons. It is more common for the method to be applied in a dynamic manner. In this case, information is gathered over a period of time, and the method is applied in a continuous or intermittent manner over a least a portion of this period of time. New information is added over a time period that can be fairly long, such as several months to a few years, and identifications occur as enough data accumulate to support them. Both newly arrived data and the results of identifications can enable further identification. For example, identification of a second parent or sibling in a family can be used to assist in identification of additional siblings. Newly arrived data can also lead to the exclusion of some possible identifications. For example, the identification of an unidentified human remain excludes the identification of this remain as originating from a different person.

In any of the methods described herein, in addition to DNA profile information, non-DNA forensic information can be used to filter or exclude a set of unknown biological specimens to include those which fit one or more requirements specific to the missing individual or to the family searching to find a missing individual. "Non-DNA forensic information" as defined herein includes, but is not limited to, dental records, skin markings (e.g., tattoos, scars), X-ray images, time of specimen collection, place of specimen collection, fingerprints, and gender as well as personal effects and clothing or fragments thereof. For example, in a group of unknown biological specimens, there may be body parts that contain tattoos. If a family is searching for a missing individual and knows that the missing individual does not have a tattoo, for example, this piece of information could exclude any unknown biological specimens which have a tattoo regardless of how well the DNA profiles seem to be related. As a second example, skeletal or other anatomical features may provide gender information. On the other hand, personal effects and the like should be relied on with some degree of risk that coincidence (or intention) placed an item proximate to certain remains.

Non-DNA forensic information also can be used to confirm the identification of an unknown biological specimen. Non-DNA forensic information can either be stored in a database which also contains DNA profile information, or in a separate database. For example, a cluster of unknown biological specimens identified as likely belonging to a missing individual may contain a jawbone which includes teeth. After carrying out a search method, dental records of a database such as dental x-rays taken from the missing individual can be used to verify that the identification is correct. It is preferred to exclude an unknown biological sample from the set of unknown biological samples after identification.

Implementation Mechanisms—Hardware Overview

Methods of the first embodiment and subsequent embodiments may be utilized in connection with computer readable media which may be provided for temporary or permanent storage in a personal computer or other computer or computer system comprising parallel processors known in the art. FIG. 7 is a block diagram that illustrates a computer system 500 upon which at least one embodiment of the invention may be implemented. Computer system 500 includes a bus 502 or other communication mechanism for communicating information, and at least one processor 504 coupled with bus 502 for processing information. Computer system 500 also includes a main memory 506, such as a random access memory ("RAM") or other dynamic storage device, coupled to bus 502 for storing information and instructions to be executed by processor 504. Main memory 506 also may be used for storing temporary variables or other intermediate information during execution of instructions to be executed by processor 504. Computer system 500 may further include a read only memory ("ROM") 508 or other static storage device coupled to bus 502 for storing static information and instructions for processor 504. A storage device 510, such as a magnetic disk, optical disk, solid-state memory, or the like, may be provided and coupled to bus 502 for storing information and instructions. Any of memories 506, 508, 510 may retain program instructions according to any embodiment of ADS or associating unknown specimens with family pedigrees.

Computer system 500 may optionally be coupled via bus 502 to a display 512, such as a cathode ray tube ("CRT"), liquid crystal display ("LCD"), plasma display, television, or the like, for displaying information to a computer user. Alternatively, information may be delivered to a computer user or another computer system or computer program using a communication interface 518. An input device 514, including alphanumeric and other keys, may be coupled to bus 502 for communicating information and command selections to processor 504. An optional type of user input device is cursor control 516, such as a mouse, trackball, stylus, or cursor direction keys for communicating direction information and command selections to processor 504 and for controlling cursor movement on display 512. This input device typically has to degrees of freedom in two axes, a first axis (e.g., x) and a second axis (e.g., y), that allows the device to specify positions in a plane. Alternatively, information and command selections may be communicated to processor 504 using a communication interface 518. Optionally, separate communication interfaces may be used to deliver information to a computer user or another computer system or computer program, and to communicate information and command selections to processor 504.

The invention is related to the use of computer system 500 for automated decision support and for identifying an unknown biological specimen as likely related to a family comprising at least a first and second family member. According to one embodiment of the invention, identifying an unknown biological specimen as likely related to a family comprising at least a first and second family member is provided by computer system 500 in response to processor 504 executing one or more sequences of one or more instructions contained in main memory 506, for example, in accordance with ADS and the flowcharts of FIGS. 4 through 6. Such instructions may be read into main memory 506 from another computer-readable medium, such as storage device 510. Execution of the sequences of instructions contained in main memory 506 causes processor 504 to perform the process steps described herein. In alternative embodiments, hard-wired circuitry may be used in place of or in combination with software instructions to implement embodiments of the invention. For example, a field-programmable gate array (FPGA) or application-specific integrated circuit (ASIC) may be used. Such a device can, for example, implement associative memory to aid in indexing, search, and retrieval of information stored in a database. A second example is use of a FPGA or ASIC to speed up calculation of a likelihood function used to rank specimens (block 140 of FIG. 4; block 240 of FIG. 5). Thus, embodiments of the invention are not limited to any specific combination of hardware circuitry and software.

The term "computer-readable medium" as used herein refers to any medium that participates in providing instructions to processor 504 for execution. Such a medium may take many forms, including but not limited to, non-volatile media, volatile media, and transmission media. Non-volatile media includes, for example, optical or magnetic disks, solid state memories, and the like, such as storage device 510. Volatile media includes dynamic memory, such as main memory 506. Transmission media includes coaxial cables, copper wire and fiber optics, including the wires that comprise bus 502. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, solid-state memory, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read. Various forms of computer readable media may be involved in carrying one or more sequences of one or more instructions to processor 504 for execution.

Computer system 500 may also include a communication interface 518 coupled to bus 502. Communication interface 518 provides a two-way data communication coupling to a network link 520 that is connected to a local network 522. For example, communication interface 518 may be an integrated services digital network ("ISDN") card or a modem to provide a data communication connection to a corresponding type of telephone line. As another example, communication interface 518 may be a network card (e.g., an Ethernet card) to provide a data communication connection to a compatible local area network ("LAN") or wide area network ("WAN"), such as the Internet or a private network. Wireless links may also be implemented. In any such implementation, communication interface 518 sends and receives electrical, electromagnetic or optical signals that carry digital data streams representing various types of information. For example, a forensic investigation may require a data communication connection to a database comprising at least DNA profile data or other forensic information. A second example is use of one or more data communication connection(s) to access at least one database used to store DNA and/or non-DNA information. Portions of the computations associated with the ADS tool and methods of FIGS. 4-6 described herein may be distributed across multiple computer systems 500 which may communicate using one or more communication interfaces 518.

Network link 520 typically provides data communication through one or more networks to other data devices. For example, network link 520 may provide a connection through local network 522 to a host computer 524 or to data equipment operated by an Internet Service Provider or private network service provider ("ISP"). An ISP in turn provides data communication services through a packet data communication network such as the worldwide network commonly referred to as the "Internet" 528 or a private network. An example of a private network is a secure data network linking law enforcement agencies and used for transmission of DNA and/or non-DNA information. Local network 522 and Internet 528 both use electrical, electromagnetic or optical signals that carry digital data streams. The signals through the various networks and the signals on network link 520 and through communication interface 518, which carry the digital data to and from computer system 500, are exemplary forms of carrier waves transporting the information.

Computer system 500 can send messages and receive data, including program code, through the network(s), network link 520 and communication interface 518. In the Internet example, a server 530 might transmit a requested code for an application program (ADS or the algorithms of FIGS. 4-6) through Internet 528, host computer 524, local network 522 and communication interface 518. In accordance with the invention, one such downloaded application provides a method of identifying an unknown biological specimen as likely related to a family comprising at least a first and second family member.

The received code may be executed by processor 504 as it is received, and/or stored in storage device 510, or other tangible computer-readable medium (e.g., non-volatile storage) for later execution. In this manner, computer system 500 may obtain application code and/or data in the form of an intangible computer-readable medium such as a carrier wave, modulated data signal, or other propagated signal.

Computer system 500 can be configured using the methods of this invention to provide services across a network to forensic personnel having client computers capable of connection to a network or other communication interface. Such services can include assistance in identification of unidentified remains and storage of DNA and non-DNA information about known individuals and missing persons and their relationships, or a family pedigree. These services can also be provided to other software, located in either computer system 500 or a separate computer system connected by a network, network link, or communication interface to computer system 500. The services can be protected using methods of authentication and/or encryption that are known in the fields of computer science and computer security in order to ensure data are neither compromised nor disclosed and to trace all accesses to the data. The computer system 500 and other associated information storage and communication components can be protected using devices and methods that are known in the fields of computer science and computer security, such as with firewalls, physical access controls, power conditioning equipment, and backup or redundant power sources. The information stored by computer system 500 and computer-readable media can be further protected using backup or redundant information storage systems, such as those that are well-known in the art. Examples include tape storage systems and RAID storage arrays.

All patents, patent applications, articles and other references cited in this disclosure and identified below are expressly incorporated herein by reference as to their entire contents.

REFERENCES

F. Dudbridge, A survey of Current Software for Linkage Analysis, Human Genomics, Vol 1, (1), 2004, 63-65.

Soledad A. Fernandez, Rohan L. Fernando, Bernt Guldbrandtsen, Liviu R. Totir, Alicia L. Carriquiry, Sampling genotypes in large pedigrees with loops. *Genet Sel, Eval.* 33 (2001) 337-367.

Howard D. Cash, Jonathon W. Hoyle, and Amy J. Sutton, "Development under extreme conditions: forensic bioinformatics in the wake of the World Trade Center disaster," genecodesforensics.com/news/CashHoyleSutton.pdf, 2003.

C. Cannings, E. A. Thompson, and H. H. Skolnick, The Recursive Derivation of Likelihoods on Complex Pedigrees. *Advances in Applied Probability*, Vol 8, No 4. (December 1976), pp 622-625.

E. Lander and P Green, Construction of Multilocus Genetic Linkage Maps in Humans. *PNAS*, Vol 84, No. 8 (Apr. 15, 1987), pp. 2363-2367.

R. C. Elston and J. Stewart, A General Model for the Genetic Analysis of Pedigree Data. *Human Heredity* 21: 523-542 (1971).

An alphabetic list of Genetic Analysis Software is available from the North Shore Long Island Jewish Research Institute in New York.

The invention claimed is:

1. A computer-implemented method of selecting and typing a subset of available family members to a missing person for DNA profiling to identify or exclude a typed unknown biological specimen as related to a family pedigree including the missing person, the computer-implemented method for implementation on computer apparatus comprising a processor, an input device coupled to the processor, an output device coupled to the processor and a memory for storing profile data obtained from said typed unknown biological specimen coupled to the processor, the computer-implemented method comprising:

(a) storing relationships in said memory between said missing person and said available family members in a family pedigree via said input device;

(b) pre-calculating and embedding in memory a plurality of bell-shaped frequency distributions of the likelihood ratios of at least six different family member combinations;

(c) using said pre-calculated and embedded frequency distributions for different family member combinations to select a particular subset of available family members for DNA typing as the selected subset;

(d) using at least one selected DNA typing technology for typing the selected subset of available family members to obtain DNA profile data and storing said DNA profile data for said selected subset in said memory;

(e) using the pedigree and said stored DNA profile data of said selected subset using a modified Elston Stewart algorithm to calculate a likelihood function value between the stored profile data obtained from said typed unknown biological specimen and said stored profile data for said selected subset of available family members via said processor; and (f) outputting a decision whether said typed unknown biological specimen likely originates from said missing person and said family pedigree or to exclude said typed unknown biological specimen as unrelated to said missing person and said family pedigree.

2. The method of claim 1 where said computer apparatus is portable.

3. The method of claim 1 additionally comprising pre-computing, via the computer processor, a portion of a pedigree likelihood ratio that a specified genetic relationship exists between the typed unknown biological specimen and said selected subset of available family members of the family pedigree, said family pedigree being stored in said memory and genetic information being obtained from known biological specimens of said selected subset of available family members.

4. The method of claim 1 further comprising determining a degree of degradation of the unknown biological specimen and, if the degree of degradation of the unknown biological specimen is high, selecting STR, Y-STR and mtDNA typing technologies for typing the unknown biological specimen.

5. The method of claim 1 further comprising storing non-DNA forensic data for the unknown biological specimen and comparing the non-DNA forensic data for the unknown biological specimen with known non-DNA forensic data for the missing person to improve the likelihood of a match between the unknown biological specimen and the missing person and the family pedigree of the missing person.

6. The method of claim 1 further comprising selecting a SNP array technology for typing the unknown biological specimen.

7. The method of claim 1 further comprising selecting STR DNA typing and a selected one of Y-STR and mtDNA typing technology for typing the unknown biological specimen.

8. The method of claim 1 further comprising selecting a subset of available family members of the family pedigree sufficient to identify the unknown biological specimen by determining an incremental value of typing a further available member of the family pedigree before typing the further available member and adding the further available family member to the selected subset.

9. Apparatus for selecting and typing a subset of available family members for DNA profiling to a missing person to identify or exclude a typed unknown biological specimen as related to a family pedigree including the missing person, the apparatus comprising (a) a processor for pre-calculating and embedding in memory a plurality of bell-shaped frequency distributions of the likelihood ratios of at least six different family member combinations and using said pre-calculated and embedded frequency distributions for different combinations of said available family members for selecting a particular subset combination of available family members for DNA typing as the selected subset;

(b) an input device coupled to the processor, the input device for receiving DNA typing information for the unknown biological specimen and for the selected subset of available family members according to at least one selected DNA typing technology;

(c) a memory for storing DNA profile data obtained from said typed unknown biological specimen and from typed subset of available family members and for storing relationships between said missing person and said available family members in a family pedigree, the DNA profile data and relationships being input via said input device, the memory being coupled to the processor; and (d) an output device, coupled to the processor, for outputting a decision whether said typed unknown biological specimen likely originates from said missing person and said family pedigree or to exclude said typed unknown biological specimen as unrelated to said missing person and said family pedigree responsive to said processor using the pedigree and said stored DNA profile date of said selected subset using a modified Elston Stewart algorithm to calculate a likelihood function value between the stored DNA profile data obtained from the typed unknown biological specimen and said stored DNA profile data for said selected subset of available family members.

10. The apparatus of claim 9 wherein said apparatus is portable and adapted for use at a site of a disaster.

11. The apparatus of claim 9 further comprising a communications interface coupled to the processor and to the memory, the communications interface for receiving DNA profile data from a remote database.

12. The apparatus of claim 9 further comprising a communications interface coupled to the processor and to the memory, the communications interface for transmitting DNA profile data to a remote database.

13. The apparatus of claim 9 wherein the input device comprises a means for typing an unknown biological specimen according to STR typing technology and one of Y-STR and mtDNA typing technologies.

* * * * *